United States Patent

Schickfluss

[11] 4,007,213
[45] Feb. 8, 1977

[54] PROCESS FOR PREPARING 1-(N-β-CYANETHYLAMINO)-3-ACYLAMINOBENZENES

[75] Inventor: Rudolf Schickfluss, Frankfurt am Main, Germany

[73] Assignee: Hoechst Aktiengesellschaft, Frankfurt am Main, Germany

[22] Filed: Apr. 27, 1976

[21] Appl. No.: 680,706

[30] Foreign Application Priority Data

Apr. 29, 1975 Germany .......................... 2519002

[52] U.S. Cl. .......................... 260/465 D; 260/207; 260/207.1
[51] Int. Cl.² ..................................... C07C 121/78
[58] Field of Search .................... 260/465 D, 465 E

[56] References Cited

UNITED STATES PATENTS 3,231,601  1/1966  Peterli .............................. 260/465
3,496,213  2/1970  Ross ................................ 260/465

Primary Examiner—Lewis Gotts
Assistant Examiner—Dolph H. Torrence
Attorney, Agent, or Firm—Curtis, Morris & Safford

[57] ABSTRACT

Process for the manufacture of 1-(N-β-cyanethylamino)-3-acylaminobenzenes of the formula (1)

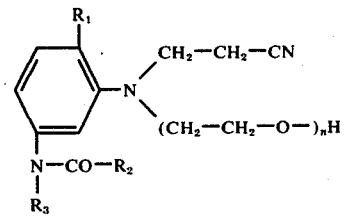

in which $R_1$ represents hydrogen, methyl or alkoxy of 1 to 4 carbon atoms, $R_2$ represents hydrogen, alkyl from 1 to 3 carbon atoms or phenyl, $R_3$ represents hydrogen or alkyl from 1 to 3 carbon atoms, and $n$ represents the integer 0 or 1, which comprises reacting 1 mole of an amino of the formula (2)

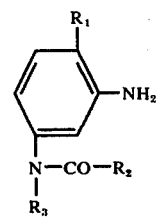

in which $R_1$, $R_2$ and $R_3$ are defined as above, with 1 to 1.75 moles of acrylonitrile between 70° and 150° C in water with the addition of 1 to 30% by weight of an organic carboxylic acid or carbonic acid, and oxethylating the compound at the said formula (1) obtained, if $n$ stands for the integer 0, without or after isolation, with 1 to 10 moles of ethylene oxide between 50° and 100° C.

4 Claims, No Drawings

PROCESS FOR PREPARING 1-(N-β-CYANETHYLAMINOL-3-ACYLAMINOBEN-ZENES

The present invention relates to an improved process for the manufacture of 1-(N-β-cyanethylamino)-3-acylaminobenzenes of the formula (1)

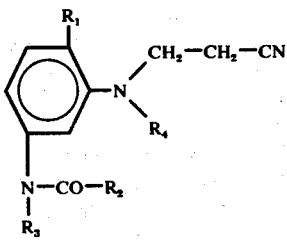

in which $R_1$ represents hydrogen, methyl or alkoxy of from 1 to 4 carbon atoms, $R_2$ represents hydrogen, alkyl from 1 to 3 carbon atoms or phenyl, $R_3$ represents hydrogen or alkyl from 1 to 3 carbon atoms, and $R_4$ represents hydrogen or oxethyl, which comprises reacting amino compounds of the formula (2)

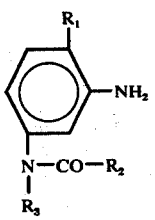

in which $R_1$, $R_2$ and $R_3$ are defined as above, in water with the addition of 1 to 30% by weight of organic carboxylic acids, preferably saturated carboxylic acids or carbonic acid with 1 to 1.75 mole of acrylonitrile, at a temperature from 70° to 150° C and optionally oxethylating the compounds obtained of formula (1), in which $R_4$ represents hydrogen without or after isolation with 1 to 10 moles of ethylene oxide at a temperature from 50° to 100° C.

It is known that aliphatic and aromatic amines may be reacted with acrylonitrile to yield the corresponding N-β-cyanethylamines. In this process aromatic amines show a highly inert reaction with acrylonitrile because of their weaker basicity, in contrast to aliphatic amines. For attaining a satisfactory reaction special catalysts and solvents must be used. Aniline derivatives, for example may be reacted with acrylonitrile in glacial acetic acid (cf. U.S. Pat. No. 2,492,972), optionally with the addition of copper salts (cf. Cookson and Mann, J. Chem. Soc. 1949, 67).

The N-cyanethylation should be performed advantageously in the presence of catalysts such as zinc chloride, zinc bromide or boron trifuoride or its etherate (cf. German Offenlegungsschrift No. 1,947,933).

U.S. Pat. No. 3,496,213 discloses an improved process, as compared to the aforesaid, for preparing N-cyanethylated aromatic amines from aromatic amines and acrylonitrile with the addition of zinc chloride in an aqueous medium.

From U.S. Pat. No. 3,231,601 it is known to cyanethylate aromatic amines with acrylonitrile in the presence of the salts of these amines with strong acids with good yields, by performing the reaction in an aqueous medium. This process however has the disadvantage that it requires a great volume of water and that the salts obtained from an aromatic amine and a strong acid do not react with acrylonitrile, so that a reduction in yield must be taken into account.

In said processes there are mainly used cyanethylated simple aromatic amines.

Finally, German Offenlegungsschrift No. 2,000,590 discloses a process in which 3-acylaminonitrobenzene is reduced with Raney-Nickel and cyanethylated with acrylonitrile without isolation, in acetic solution with the addition of Lewis acids, for example zinc chloride or zinc sulfate.

In the literature there is known little about the oxethylation of compounds having the formula (1) mentioned above, in which $R_4$ is hydrogen. Published Japanese Patent Application No. 72, 119, 79 teaches the oxethylation of monocyanethylated anilines which may be substituted by halogen atoms, alkyl or alkoxy groups, performed at a temperature from 120° to 180° without the addition of solvents.

According to the novel process described above (cyanethylation) the 1-(N-β-cyanethylamino)-3-acylaminobenzenes of formula (3)

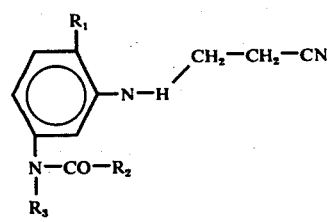

(in which $R_1$, $R_2$ and $R_3$ are defined as above), can be obtaines surprisingly in a smooth reaction and with good yields.

The compounds of formula (3) may be reacted with ethylene oxide to yield the compounds of formula (4)

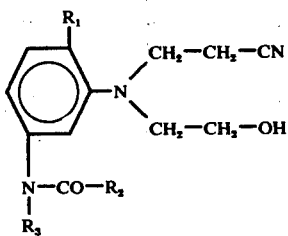

in which $R_1$, $R_2$ and $R_3$ are defined as above without or after isolation.

The novel cyanethylation process has a number of essential advantages as compared to the known processes: The waste water is not impurified with toxic ions of heavy metals, owing to the fact that there are not used Lewis acids, for example copper and zinc salts, and additional purification operations may thus be dispensed with. Technical problems due to the material used, such as corrosion problems arising in the use of Lewis acids and mineral acids are moreover avoided in the novel process. The reaction products are obtained in a good crystalline form and may thus be readily isolated. They may also be used directly in the form of the reaction solution or suspension obtained as azocomponents for preparing azo dyes or for oxethylating. In this way the technical and personal expenditure may be dispensed with and losses of material occuring when isolating can be avoided.

The N-cyanethyl-N-oxethylamines of the formula (4) may be used advantageously as azocomponents for the manufacture of azo dyes without isolation (cf. British Patents Nos. 1,053,830, 1,148,672 and 1,187,087). The novel process is, consequently, a rather interesting economical one for preparing compounds of formula (1).

Suitable aromatic amines of formula (2) for the process of the invention are, for example: 3-acetaminoaniline, 3-benzoylaminoaniline, 3-formylaminoaniline, 2-methyl-5-acetaminoaniline, 2-methyl-5-propionylaminoaniline, 2-methoxy-5-acetaminoaniline, 2-methoxy-5-formylaminoaniline, 2-methoxy-5-propionylaminoaniline, 2-methoxy-5-benzoylaminoaniline, 2-ethoxy-5-acetaminoaniline, 2-ethoxy-5-formylaminoaniline, 2-ethoxy-5-propionylaminoaniline, 2-ethoxy-5-benzoylaminoaniline, and 3-amino-1,N-methylacetanilide.

The aromatic amines of formula (2) may be used for the cyanethylation after isolation in a dry or wet form or especially advantageously without isolation in the form of their aqueous solution or suspension according to the hydrogenation described in German Offenlegungsschrift No. 2,240,849. The cyanethylation is carried out in an aqueous medium, to which from 1 to 30% by weight of organic carboxylic acids or carbonic acid, preferably from 1 to 10% by weight of glacial acetic acid have been added. Suitable carboxylic acids are besides glacial acetic acid formic acid, propionic acid and butyric acid. Mixtures of said acids may also be used.

The reaction solution should always be slightly acid during the oxethylation.

From 1 to 1.75 moles of acrylonitrile are required, in dependence of the amine used.

According to the novel process the aromatic amine is generally reacted with acrylonitrile by refluxing, preferably, however, in a closed system. Operating in a closed system is extremely advantageous, owing to the fact that the aromatic amines used in the described reaction are little reactive and sterically hindered. The reaction is performed at a temperature from 70° to 150° C, preferably from 90° to 120° C. The period of heating during the cyanethylation depends on the amine used and is generally in the range from 2 to 15 hours.

The resistance of the nitrile group in the process of the invention inspite of the long residence time in an aqueous medium at temperatures, at which a saponification already takes place according to the experiences made hitherto, to form an acid amide group is surprising.

Polymerization inhibitors such as hydroquinone may be added optionally to avoid polymerizing of the acrylonitrile. Although the aromatic amines used are only little soluble in water, dissolving intermediaries such as dispersing agents, for example, condensation products of alkyl phenols with ethylene oxide need not be used. The monocyanethylated amines of the formula (3) are generally obtained in a good crystalline form according to the process of the invention after the reaction batch has been cooled and may be isolated with a high degree of purity by suction-filtering. The yields are in the range of from 75 to 90% of the theory in dependence of the aromatic amine used and may be improved by adding mineral salts to the cooled reaction batch or by evaporating a part of the aqueous reaction medium to amount up to 95% of the theory.

It is often advantageous to renounce to an isolation of the mono-cyanethylated amines of the formula (3) and to submit the suspensions obtained of these amines directly to a further reaction. These suspensions may be directly used advantageously as azocomponents for the manufacture of azo dyes, especially for the manufacture of blue monoazo dyes.

The suspensions of the mono-cyanethylated aromatic amines obtained in the cyanethylation according to the invention of the formula (3) are especially appropriate for the manufacture of compounds of the formula (4) by oxethylation. In this process ethylene oxide is introduced directly into the suspension of the mono-cyanethylated aromatic amines of the formula (3). A quantity of from 1 to 10 moles of ethylene oxide is required, in dependence of the aromatic amine used each time, owing to the fact that the amines concerned are little reactive, slightly basic compounds, especially due to the nitrile group in $\beta$-position, and that a reaction of the ethylene oxide is highly hindered sterically. Possibly escaping ethylene oxide may be collected in a recipient. The reaction is terminated within 2 to 20 hours, generally within 5 to 10 hours. The reaction temperature is maintained at a level of from 50° to 100° C, preferably of from 75° to 85° C during the oxethylation. By isolating the oxethylation products thus prepared it can be seen that they are obtained in a very good yield, amounting to about 95% of the theory. After oxethylating an aqueous solution of the aromatic amines of formula (4) is obtained being of great importance as azocomponents, especially for the manufacture of blue monoazo dyes. Isolating of the amines obtained of formula (4) is not required. It is even of great advantage that the solutions obtained of these azocomponents may be directly used for the manufacture of azo dyes.

The following examples illustrate the invention. The parts are to the parts by volume as the gram to the milliliter.

EXAMPLE 1

300 parts of 3-aminoacetanilide were suspended in 1000 parts by volume of water and 20 parts by volume of glacial acetic acid in an agitator autoclave having a capacity of 2500 parts by volume. 159 parts by volume of acrylonitrile were added thereto and the batch was maintained in the autoclave at a temperature of about 100° C. After cooling a suspension of 1-(N-$\beta$-cyanethylamino)-3-acetaminobenzene was obtained, which could be directly further reacted. By filtering off with suction the cyanethylation product 368 parts of very pure 1-(N-$\beta$-cyanethylamino)-3-acetaminobenzene of the formula

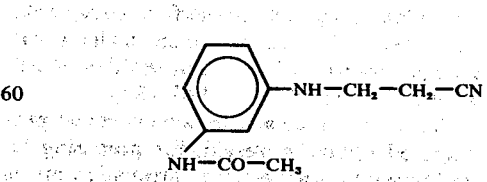

were obtained, which corresponded to a yield of 90.6% of the theory. The yield may be improved by salting out or by concentrating the reaction solution by about 3 to 4%. The melting point of the isolated product was 117°

C. 110 parts of ethylene oxide were introduced into the suspension obtained in the aforesaid manner, after having flushed with nitrogen, at a temperature of from 70° to 90° C within a period of 8 hours. Small amounts of escaping ethylene oxide were seized in a trap. Thus a product reacted to a large extent was obtained having the formula

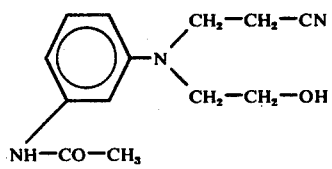

being present in the reaction solution in a dissolved state. It may be directly used in this form for a coupling reaction in the preparation of azo dyes.

EXAMPLE 2

164 parts of 2-amino-4-acetaminotoluene were suspended in 550 parts by volume of water and 15 parts by volume of formic acid in an agitator autoclave having a capacity of 1000 parts by volume. 80 parts by volume of acrylonitrile were added thereto. The batch was maintained at a temperature of about 130° C in the autoclave. After cooling a suspension of 2-(N-β-cyanethylamino)-4-acetamino-toluene was obtained having the formula

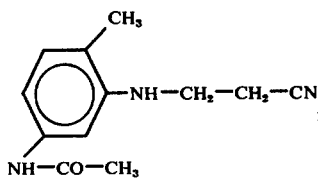

which could be directly further reacted. By filtering off with suction the cyanethylation product 178 parts of pure 2-(N-cyanethylamino)-4-acetaminotoluene were obtained which corresponded to a yield of 82% of the theory. The melting point of the isolated product was from 143° to 144° C.

After having flushed with nitrogen 220 parts of ethylene oxide were introduced directly into the suspension prepared in the aforesaid manner at a temperature from 70° to 80° C within 8 hours. Small quantities of escaping ethylene oxide were collected in a trap. Thus a product reacted to a large extent was obtained having the formula

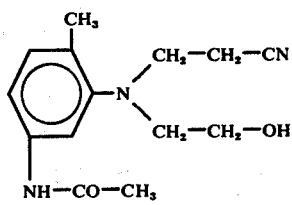

which was present in a dissolved state in the reaction solution and can be directly used for the coupling reaction in the preparation of azo dyes.

EXAMPLE 3

A suspension of 270 parts of 2-amino-4-acetaminoanisol in 1000 parts by volume of water as obtained in the hydrogenation of the corresponding nitro compound according to German Offenlegungsschrift No. 2,240,849 was given into an agitator autoclave having a capacity of 2000 parts by volume, 40 parts by volume of glacial acetic acid and 140 parts by volume of acrylonitrile were added to this suspension. The reaction batch was kept in the autoclave while stirring at a temperature of 110° C for a period of 7 hours. After cooling a suspension of 2-N-β-cyanethylamino-4-acetaminoanisol was obtained having the formula

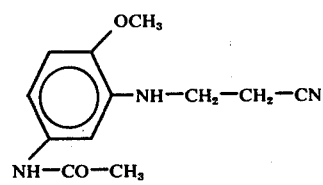

which could be further reacted. By suction-filtering the cyanethylation product 273 parts of pure 2-(N-cyanethylamino)-4-acetaminoanisol were obtained, which corresponded to a yield of 78% of the theory. The yield may be improved by up to 10% by salting out. The melting point of the isolated product was 121° C.

After having flushed with nitrogen 330 parts of ethylene oxide were directly introduced into the suspension obtained, at a temperature of about 80° C within a period of 10 hours. Small quantities of escaping ethylene oxide were collected by means of a trap. Thus a product was obtained being converted to a large extent and having the formula

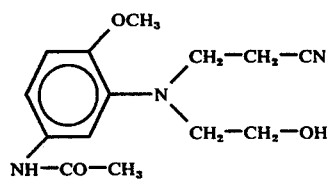

which was present in a dissolved state in the reaction solution and can be directly used in this form for the coupling reaction in the manufacture of azo dyes.

EXAMPLE 4

In an agitator autoclave of 2000 parts by volume there were suspended while stirring 291 parts of 2-amino-4-acetaminophenetol in 1000 parts by volume of water and 50 parts by volume of glacial acetic acid. 140 parts by volume of acrylonitrile were added and the batch was kept at a temperature of about 100° C in the autoclave. After cooling a suspension of 2-(N-β-cyanethylamino)-4-acetaminophenetol was obtained having a melting point of 129° C and the formula

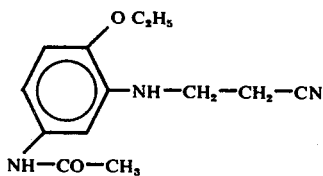

330 parts by volume of ethylene oxide were directly introduced into the suspension thus obtained, after having flushed with nitrogen, at a temperature of about 80° C within a period of 10 hours. Small quantities of escaping ethylene oxide were collected by means of a trap. Thus a product reacted to a large extent was obtained having the formula

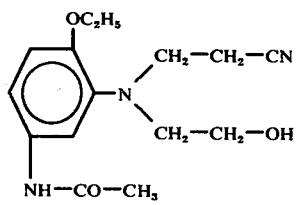

which was present in the reaction solution in a dissolved state and can be directly used in this form for the coupling reaction in the manufacture of azo dyes.

EXAMPLE 5

In an agitator autoclave of 4000 parts by volume there were suspended 540 parts of 2-amino-4-acetaminoanisol in 2000 parts by volume of water and 50 parts by volume of glacial acetic acid. 256 parts by volume of acrylonitrile were added to this suspension and the batch was stirred for 9 hours at a temperature of 100° C. Then the reaction mixture was allowed to cool and a suspension of 2-N-β-cyanethylamino-4-acetaminoanisol was obtained of the formula

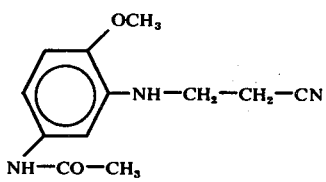

By suction filtering the cyanethylation product 562 parts of 2-(N-β-cyanethylamino)-4-acetaminoanisol were obtained which corresponded to a yield of 80.4% of the theory. The melting point of the isolated product was 121° C.

After having flushed with nitrogen 660 parts of ethylene oxide were introduced into the suspension thus obtained, at a temperature of 80° C within a period of 10 hours. Small quantities of escaping ethylene oxide were collected by means of a trap. Thus a product converted to a large extent was obtained having the formula

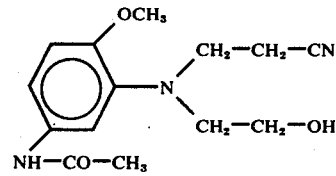

which was present in the reaction solution in a dissolved state and can be directly used for the coupling reaction in the manufacture of azo dyes.

EXAMPLE 6

164 parts of 2-amino-4-acetaminotoluene in 550 parts by volume of water were suspended while stirring in an agitator autoclave of 1000 parts by volume. The pH of the suspension was adjusted to a value of from 6.5 to 5.5 by introducing carbonic acid ($CO_2$). 80 parts by volume of acrylonitrile were added. The batch was kept in the autoclave at a temperature of about 100° C for a period of 10 hours. After cooling a suspension of 2-(N-β-cyanethylamino)-4-acetaminotoluene was obtained which could be directly further reacted. By suction-filtering the cyanethylation product 174.5 g of pure 2-(N-β-cyanethylamino)-4-acetaminotoluene were obtained having the formula

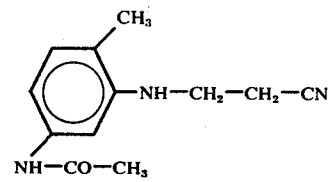

which corresponded to a yield of 80.4% of the theory. The melting point of the isolated product was 143° C.

220 parts of ethylene oxide were introduced into the suspension obtained as described above, at a temperature of from 70° to 80° C within a period of 8 hours, after having flushed with nitrogen. Small quantities of escaping ethylene oxide were collected by means of a trap. In this way a product converted to a large extent was obtained having the formula

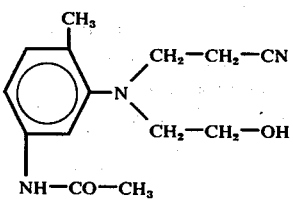

which was present in the reaction solution in a dissolved state and can be directly used in this form for the coupling reaction in the manufacture of azo dyes.

EXAMPLE 7

164 parts of 3-amino-1,N-methylacetanilide in 650 parts by volume of water and 30 parts by volume of glacial acetic acid were suspended while stirring in an agitator autoclave of 1000 parts by volume. 80 parts by volume of acrylonitrile were added to the suspension obtained and the batch was stirred for 10 hours at a temperature of 100° C. After cooling a suspension of 3-N-β-cyanethylamino-1,N-methylacetaniline was obtained having the formula

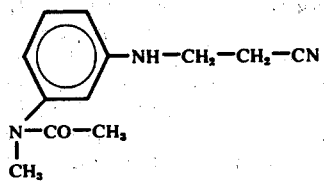

By suction-filtering the cyanethylation product 176 parts of 3-N-β-cyanethylamino-1,N-methylacetanilide were obtained, which corresponded to a yield of 81% of the theory.

220 parts of ethylene oxide were directly introduced into the suspension prepared in the aforesaid manner after having flushed with nitrogen, at a temperature of from 70° to 80° C within a period of 8 hours. Small quantities of escaping ethylene were collected by means of a trap. In this way a product converted to a large extent was obtained having the formula

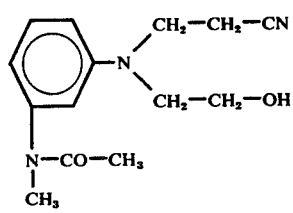

which was present in the reaction solution in a dissolved state and can be directly used in this form for the coupling reaction in the manufacture of azo dyes.

EXAMPLE 8

In an agitator autoclave having a capacity of 1000 parts by volume there were suspended while stirring 136 parts of 3-aminoformanilide in 550 parts by volume of water and 20 parts by volume of glacial acetic acid. 80 parts by volume of acrylonitrile were added thereto. The batch was kept in the autoclave at a temperature of about 110° C for a period of 10 hours. After cooling a suspension of 3-(N-β-cyanethylamino)-formanilide was obtained having the formula

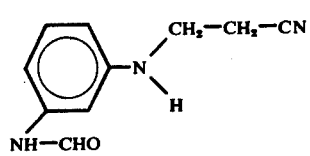

which could be directly further reacted as described hereafter.

130 parts of ethylene oxide were introduced into the suspension obtained after having flushed with nitrogen, at a temperature of from 70° to 80° C within a period of 8 hours. In this way a product converted to a large extent was obtained, namely the 3-(N-β-cyanethyl-N-oxethyl)aminoformanilide having the formula

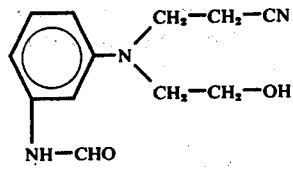

which was present in the reaction solution in a dissolved state and can be directly used in this form for the coupling reaction in the manufacture of azo dyes.

EXAMPLE 9

212 parts of 3-aminobenzanilide in 600 parts by volume of water and 20 parts by volume of glacial acetic acid were suspended while stirring in an agitator autoclave having a capacity of 1000 parts by volume. 80 parts by volume of acrylonitrile were added thereto. The batch was kept in the autoclave at a temperature of about 110° C for 10 hours. After cooling a suspension of 3-(N-β-cyanethylamino)-benzanilide was obtained having the formula

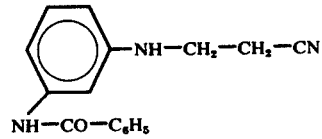

which could be directly further reacted as described hereafter.

220 parts of ethylene oxide were introduced into the suspension obtained at a temperature of 80° C after having flushed with nitrogen, within a period of 8 hours.

In this way a product converted to a large extent, namely the 3-(N-β-cyanethyl-N-aminobenzanilide) was obtained having the formula

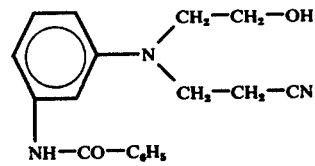

which was present in the reaction solution in a dissolved state and can be directly used in this form for the coupling reaction in the manufacture of azo dyes.

I claim:
1. Process for the manufacture of 1-(N-β-cyanethylamino)-3-acylaminobenzenes of the formula (1)

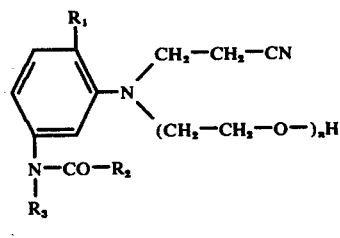

(1)

in which $R_1$ represents hydrogen, methyl or alkoxy of 1 to 4 carbon atoms, $R_2$ represents hydrogen, alkyl from 1 to 3 carbon atoms or phenyl, $R_3$ represents hydrogen or alkyl from 1 to 3 carbon atoms, and $n$ represents the integer 0 or 1, which comprises reacting 1 mole of an amine of the formula (2)

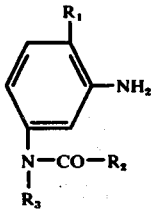
(2)

in which $R_1$, $R_2$ and $R_3$ are defined as above, with 1 to 1.75 moles of acrylonitrile between 70° and 150° C in water with the addition of 1 to 30% by weight of an organic carboxylic acid or carbonic acid, and oxethylating the compound of the said formula (1) obtained, if $n$ stands for the integer 0, without or after isolation, with 1 to 10 moles of ethylene oxide between 50° and 100° C.

2. The process as claimed in claim 1, wherein the reaction with the acrylonitrile is performed with the addition of formic acid, acetic acid, propionic acid or butyric acid or mixtures thereof as carboxylic acid.

3. The process as claimed in claim 1, wherein the 1-(N-β-cyanethylamino)-3-acylaminobenzene compound obtained by the reaction of the amino of the said formula (2) with the acrylonitrile is-before the reaction with the ethylene oxide-further precipitated and isolated by the addition of inorganic salts.

4. The process as claimed in claim 1, wherein the 1-(N-β-cyanethylamino)-3-acylaminobenzene compound is - before the reaction with the ethylene oxide — concentrated and isolated by evaporating a part of the aqueous reaction medium.

* * * * *

UNITED STATES PATENT AND TRADEMARK OFFICE
CERTIFICATE OF CORRECTION

PATENT NO. : 4,007,213
DATED : February 8, 1977
INVENTOR(S) : Rudolf Schickfluss It is certified that error appears in the above-identified patent and that said Letters Patent are hereby corrected as shown below:

In the Heading, Item [54], change "CYANETHYLAMINOL" to

--CYANETHYLAMINO)--.

Signed and Sealed this

Nineteenth Day of April 1977

[SEAL]

Attest:

RUTH C. MASON
Attesting Officer

C. MARSHALL DANN
Commissioner of Patents and Trademarks